United States Patent
Guggenheimer et al.

(10) Patent No.: US 10,631,894 B2
(45) Date of Patent: Apr. 28, 2020

(54) TISSUE-REMOVING CATHETER, TISSUE-REMOVING ELEMENT, AND METHOD OF MAKING SAME

(71) Applicant: Covidien LP, Mansfield, MA (US)

(72) Inventors: Ethan Guggenheimer, Minnetonka, MN (US); Benjamin Fruland, Blaine, MN (US); Victoria Schuman, Minneapolis, MN (US); Virgil Koski, Columbia Heights, MN (US)

(73) Assignee: Covidien LP, Mansfield, MA (US)

( * ) Notice: Subject to any disclaimer, the term of this patent is extended or adjusted under 35 U.S.C. 154(b) by 437 days.

(21) Appl. No.: 15/208,081

(22) Filed: Jul. 12, 2016

(65) Prior Publication Data

US 2017/0014146 A1    Jan. 19, 2017

Related U.S. Application Data

(60) Provisional application No. 62/192,600, filed on Jul. 15, 2015.

(51) Int. Cl.
*A61B 17/3207* (2006.01)
*A61B 17/00* (2006.01)

(52) U.S. Cl.
CPC ........ *A61B 17/320783* (2013.01); *A61B 17/320758* (2013.01); *A61B 2017/00526* (2013.01); *A61B 2017/320791* (2013.01)

(58) Field of Classification Search
CPC .... A61B 17/320758; A61B 17/320783; A61B 17/3207; A61B 17/1615; A61B 17/3205; A61B 17/320725; A61B 2017/00685; A61B 2017/320775; A61B 2017/320791; A61B 2017/22039; A61B 2017/22094; A61B 2017/22044; A61B 2017/320741; A61B 2017/00309; A61B 2017/320004; A61M 25/0152; A61N 2001/0578

See application file for complete search history.

(56) References Cited

U.S. PATENT DOCUMENTS

| | | |
|---|---|---|
| 4,925,216 A | 5/1990 | Steer |
| 5,084,010 A | 1/1992 | Plaia et al. |
| 5,351,595 A | 10/1994 | Johnston |

(Continued)

FOREIGN PATENT DOCUMENTS

| | | |
|---|---|---|
| EP | 1 058 516 B1 | 11/2005 |
| EP | 1 158 910 B1 | 10/2007 |

(Continued)

*Primary Examiner* — Ryan J. Severson
*Assistant Examiner* — Mohamed G Gabr (57) ABSTRACT

A tissue-removing catheter includes a tissue-removing element operably connected to a drive shaft for rotation of the tissue-removing element about an axis of rotation in a cutting direction. The tissue-removing element is, in some embodiments, an integrally formed one-piece body. The tissue-removing element has a tissue-removing head that includes a plurality of shearing members spaced apart around the axis of rotation. Channels separate the plurality of shearing members and extend through the radially outer surface of the tissue-removing head. In some embodiments, the shearing members include respective wedge portions that hook and cleave tissue as the tissue-removing element rotates.

17 Claims, 11 Drawing Sheets

(56) References Cited

U.S. PATENT DOCUMENTS

| | | |
|---|---|---|
| 5,507,760 A | 4/1996 | Wynne et al. |
| 5,651,781 A | 7/1997 | Grace |
| 5,919,203 A | 7/1999 | Husted et al. |
| 6,136,014 A | 10/2000 | Sirimanne et al. |
| 6,451,036 B1 | 9/2002 | Heitzmann et al. |
| 6,623,496 B2 | 9/2003 | Snow et al. |
| 6,666,874 B2 | 12/2003 | Heitzmann et al. |
| 6,685,707 B2 | 2/2004 | Roman et al. |
| 6,997,934 B2 | 2/2006 | Snow et al. |
| 7,171,798 B1 | 2/2007 | Bernardy |
| 7,172,610 B2 | 2/2007 | Heitzmann et al. |
| 7,666,134 B2 | 2/2010 | Eriksson et al. |
| 7,842,058 B2 | 11/2010 | Simpson et al. |
| 8,070,762 B2 | 12/2011 | Escudero et al. |
| 8,215,533 B2 | 7/2012 | Viola |
| 8,236,016 B2 | 8/2012 | To et al. |
| 8,262,585 B2 | 9/2012 | Thompson et al. |
| 8,308,746 B2 | 11/2012 | Pravong et al. |
| 8,337,516 B2 | 12/2012 | Escudero et al. |
| 8,361,094 B2 | 1/2013 | To et al. |
| 8,469,981 B2 | 6/2013 | Robertson et al. |
| 8,475,483 B2 | 7/2013 | Schmitz et al. |
| 8,531,064 B2 | 9/2013 | Robertson et al. |
| 2002/0077642 A1 | 6/2002 | Patel et al. |
| 2007/0266833 A1 | 11/2007 | Radziszewski et al. |
| 2010/0256527 A1 | 10/2010 | Lippert et al. |
| 2010/0256528 A1 | 10/2010 | Lippert et al. |
| 2010/0256601 A1 | 10/2010 | Lippert et al. |
| 2010/0256602 A1 | 10/2010 | Lippert et al. |
| 2010/0256606 A1 | 10/2010 | Lippert et al. |
| 2011/0054507 A1 | 3/2011 | Batten et al. |
| 2011/0098711 A1 | 4/2011 | Batten et al. |
| 2012/0022564 A1 | 1/2012 | Batten et al. |
| 2012/0046679 A1 | 2/2012 | Patel et al. |
| 2012/0296277 A1 | 11/2012 | Summerville et al. |
| 2013/0096587 A1 | 4/2013 | Smith et al. |
| 2014/0128893 A1* | 5/2014 | Guggenheimer ............ A61B 17/320758 606/159 |
| 2014/0171987 A1* | 6/2014 | Schneider .......... A61B 17/3207 606/159 |

FOREIGN PATENT DOCUMENTS

| | | |
|---|---|---|
| EP | 1 870 044 B1 | 7/2009 |
| EP | 1 957 134 B1 | 8/2011 |
| WO | 2007/067449 A2 | 6/2007 |
| WO | 2010/077692 A2 | 7/2010 |
| WO | 2010/121172 A1 | 10/2010 |
| WO | 2012/003430 A2 | 1/2012 |
| WO | 2013/049734 A1 | 4/2013 |

* cited by examiner

TISSUE-REMOVING CATHETER, TISSUE-REMOVING ELEMENT, AND METHOD OF MAKING SAME

CROSS-REFERENCE TO RELATED APPLICATIONS

The present application claims the benefit of U.S. Provisional Ser. No. 62/192,600, filed Jul. 15, 2015, the entirety of which is hereby incorporated by reference.

FIELD OF THE DISCLOSURE

The present disclosure generally relates to a tissue-removing catheter, tissue-removing element thereof, and method of making the tissue-removing element.

BACKGROUND OF THE DISCLOSURE

Catheters are used to remove unwanted tissue from the body. As an example, atherectomy catheters are used to remove material from a blood vessel to open the blood vessel and improve blood flow through the vessel.

SUMMARY OF THE DISCLOSURE

A tissue-removing catheter includes a tissue-removing element operably connected to a drive shaft for rotation of the tissue-removing element about an axis of rotation in a cutting direction. The tissue-removing element is, in some embodiments, an integrally formed one-piece body. The tissue-removing element has a tissue-removing head that includes a plurality of shearing members spaced apart around the axis of rotation. Channels separate the plurality of shearing members and extend through the radially outer surface of the tissue-removing head. In some embodiments, the shearing members include respective wedge portions that hook and cleave tissue as the tissue-removing element rotates.

Other objects and features will be in part apparent and in part pointed out hereinafter.

BRIEF DESCRIPTION OF THE DRAWINGS

Corresponding reference characters indicate corresponding parts throughout the drawings.

DETAILED DESCRIPTION

Referring now to the drawings, several embodiments of a tissue-removing catheter for removing tissue from a body lumen are disclosed. In particular, the illustrated catheter embodiments are suitable for removing tissue from a body lumen wall, and are particularly suitable for removing (i.e., excising) plaque tissue from a vessel wall (e.g., peripheral arterial or peripheral venous wall). Features of the disclosed embodiments, however, may also be suitable for treating chronic total occlusion (CTO) of blood vessels, particularly peripheral arteries, and stenoses of other body lumens and other hyperplastic and neoplastic conditions in other body lumens, such as the ureter, the biliary duct, respiratory passages, the pancreatic duct, the lymphatic duct, and the like. Neoplastic cell growth will often occur as a result of a tumor surrounding and intruding into a body lumen. Removal of such material can thus be beneficial to maintain patency of the body lumen. While the remaining discussion is directed toward catheters for removing tissue from and penetrating occlusions in blood vessels (e.g., atheromatous or thrombotic occlusive material in an artery, or other occlusions in veins), it will be appreciated that the teachings of the present disclosure apply equally to other types of tissue-removing catheters, including, but not limited to, catheters for penetrating and/or removing tissue from a variety of occlusive, stenotic, or hyperplastic material in a variety of body lumens.

Figure 1:
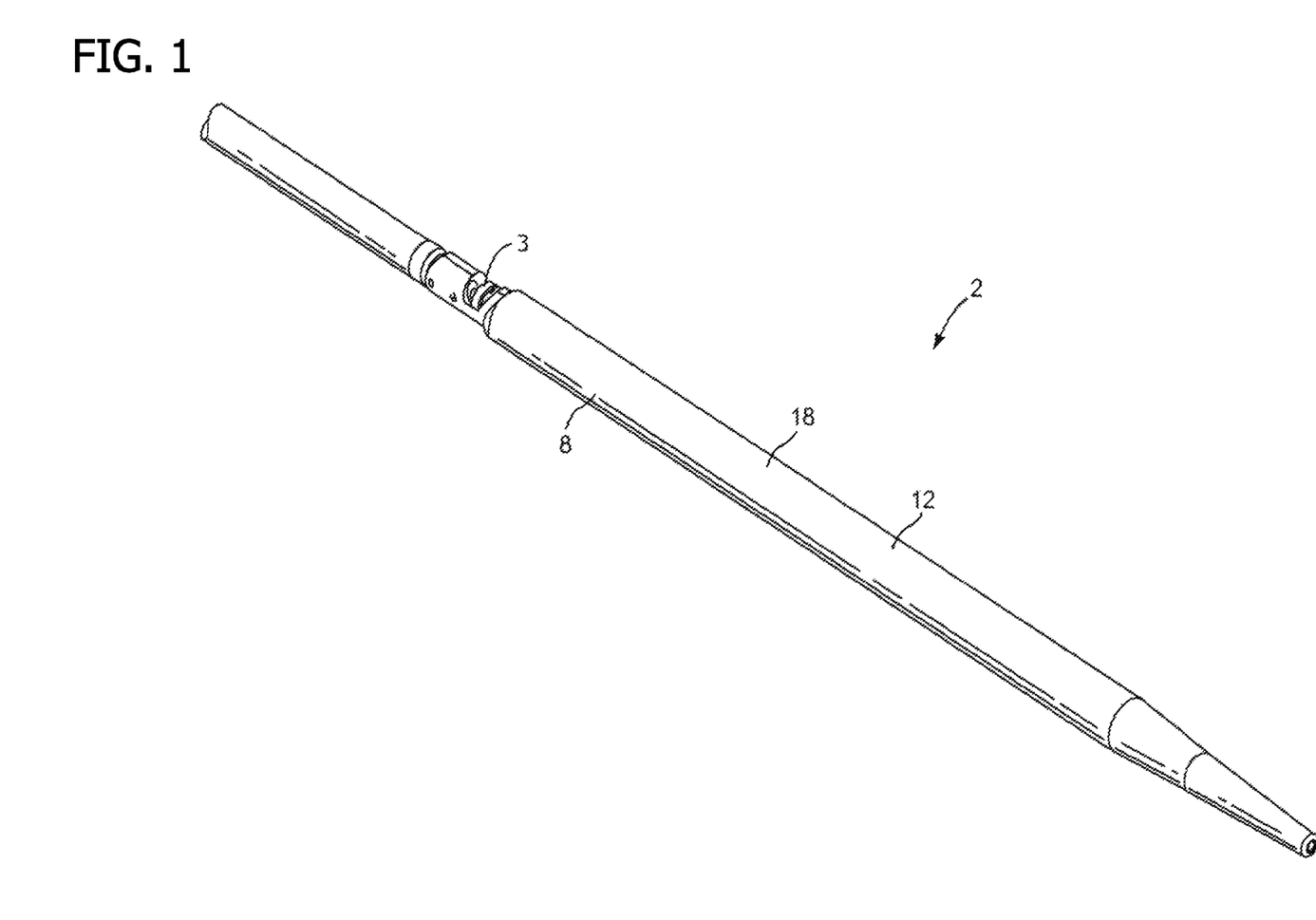
FIG. 1 is a perspective of a distal end of an atherectomy catheter.
Figure 2:
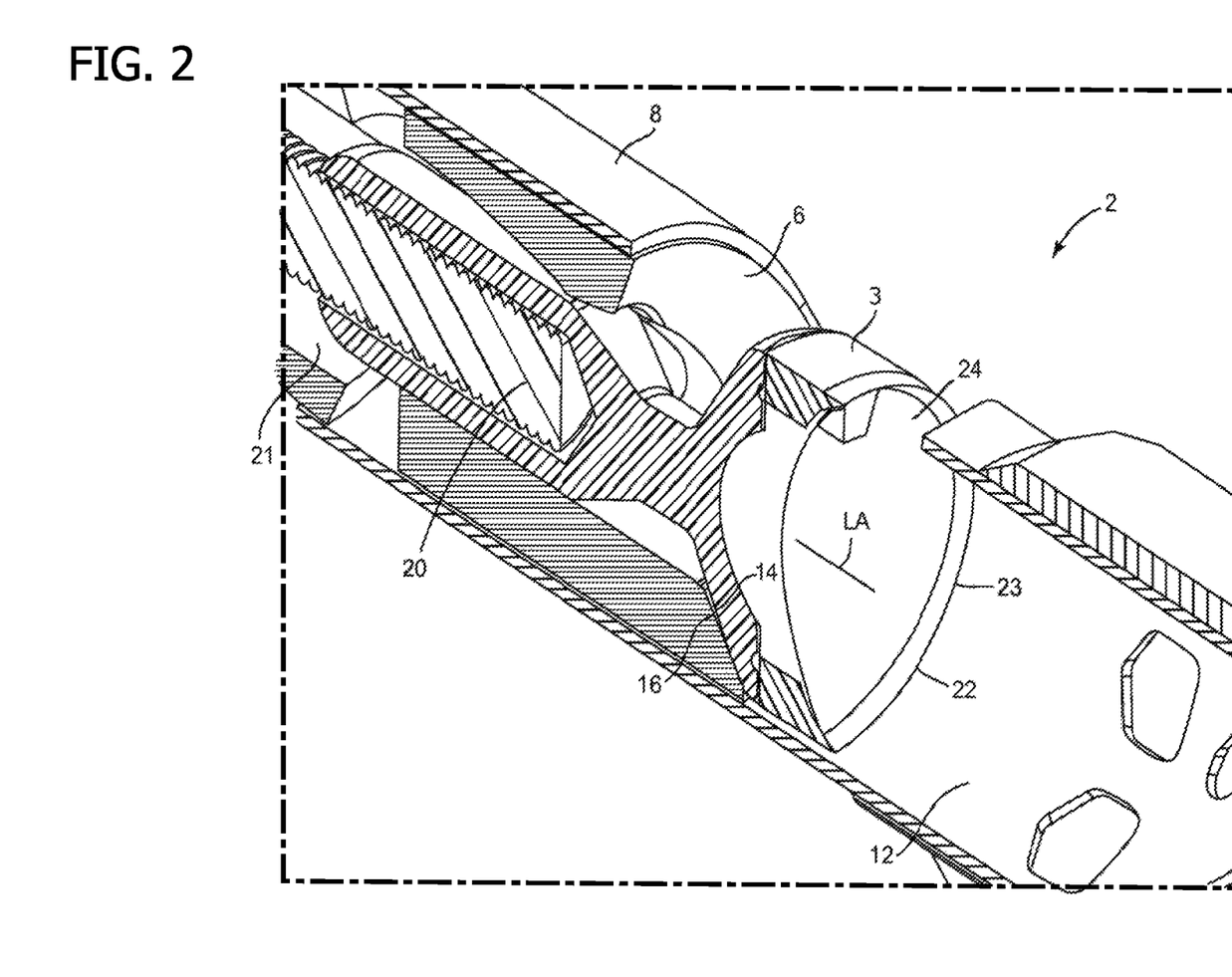
FIG. 2 is an enlarged fragmentary section of the atherectomy catheter of FIG. 1, illustrating one embodiment of a tissue-removing element in a stowed position.
Figure 3:
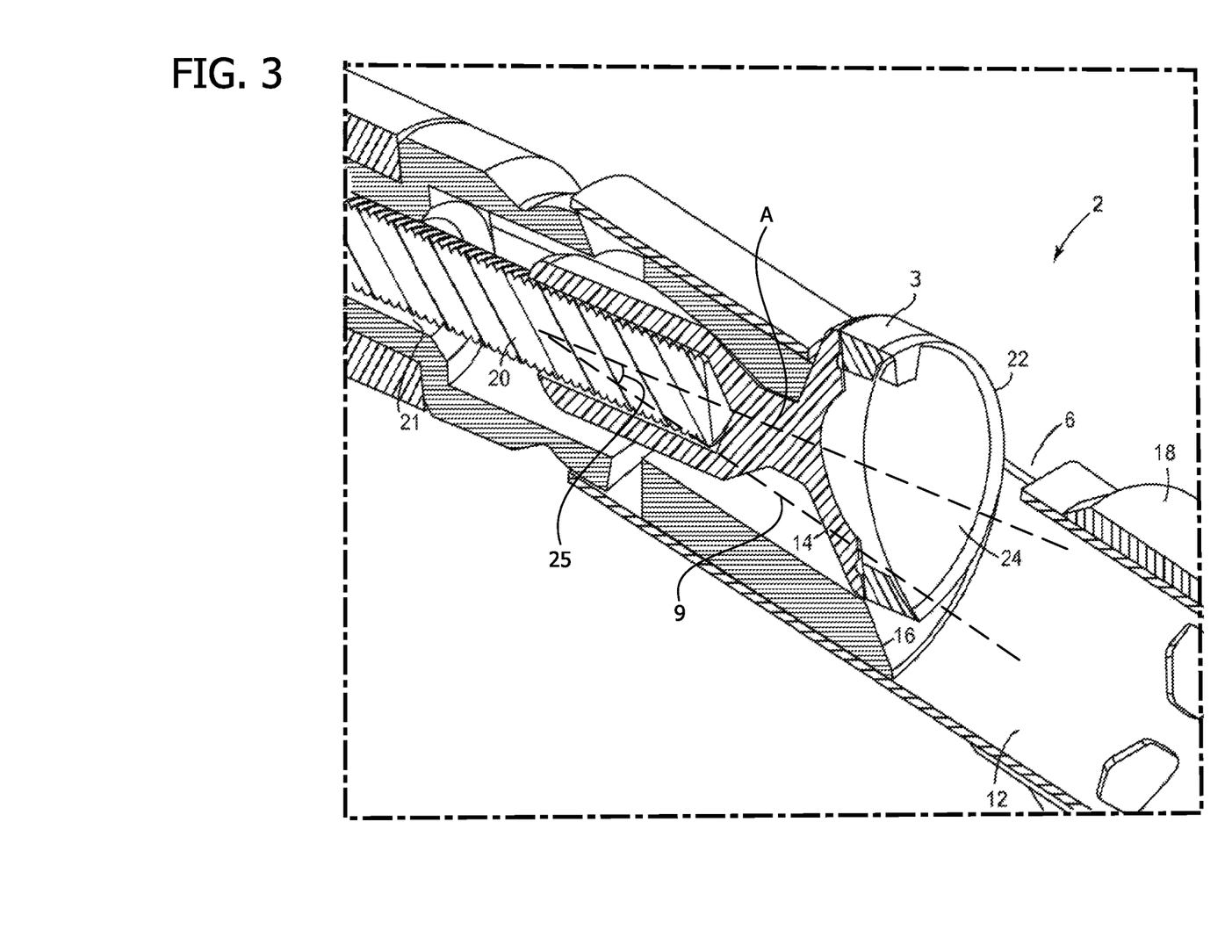
FIG. 3 is the enlarged fragmentary section of FIG. 1, illustrating the tissue-removing element in a deployed position.

Referring to FIGS. 1 to 3, an atherectomy catheter 2 (broadly, a "tissue-removing catheter"), which has a tissue-removing element 3 (broadly, a "tissue-removing element"), is used to cut material from a body lumen. The tissue-removing element 3 illustrated in FIGS. 1 to 3 is a conventional tissue-removing element. As will be explained below, tissue-removing element embodiments described in the present application are suitable replacements for the conventional tissue-removing element 3. That is, the tissue-removing element embodiments described herein below are suitable for use with the illustrated catheter 2 in place of the conventional tissue-removing element 3. The catheter has an elongate body 8 having distal and proximal portions and sized and shaped for insertion into a body lumen of a subject. The tissue-removing element 3 is movable between a stored position (FIG. 2) and a cutting position (FIG. 3) relative to a window or opening 6 in the catheter body 8 adjacent the distal portion. The tissue-removing element 3 moves outwardly relative to the opening 6 so that an exposed portion of the element 3 extends outside the body 8 through the opening 6. The tissue-removing element 3 may be positioned relative to the body 8 and opening 6 so that less than 90 degrees of the tissue-removing element 3 is exposed to cut tissue. Of course, more of the tissue-removing element 3 may be exposed without departing from numerous aspects of the invention. Preferably, when the tissue-removing element 3 is in the cutting position, a longitudinal axis A of the tissue-removing element 3 is oriented at an attack angle 25 relative a longitudinal axis 9 of a leading portion of the catheter body 8.

Catheter 2 may have a maximum size of 3, 4, 5, 6, 7, 8, 9, 10, or 12 French (1, 1.3, 1.7, 2, 2.3, 2.7, 3, 3.3, or 4 mm) and may have a working length ranging of 20, 30, 40, 60, 80, 100, 120, 150, 180 or 210 cm depending on the requirements of the anatomical location in which use of the catheter is contemplated.

In the illustrated embodiment, the catheter 2 is moved distally through a vessel with the tissue-removing element 3 in the working or cutting position as described in further detail below. As the catheter 2 moves through the blood vessel, the tissue is cut by the tissue-removing element 3 and is directed into a tissue chamber 12 positioned distal to the tissue-removing element 3. The tissue chamber 12 may be somewhat elongate to accommodate the tissue that has been cut.

Referring to FIG. 3, the illustrated tissue-removing element 3 is moved proximally from the stored position so that a cam surface 14 on the tissue-removing element 4 engages a ramp 16 on the body 8 of the catheter 2. The interaction between the cam surface 14 and the ramp 16 causes the tissue-removing element 3 to move to the cutting position and also causes a tip 18 to deflect which tends to move the tissue-removing element 3 toward the tissue to be cut. The tissue-removing element 3 may be deployed in other ways without departing from the scope of the present invention.

The tissue-removing element 3 is coupled to a drive shaft 20 that extends through a lumen 21 in the catheter 2. The tissue-removing element 3 is rotated about an axis of rotation A in a rotational direction R when the drive shaft rotates about its longitudinal axis. The tissue-removing element 3 may be rotated at about 1 to 160,000 rpm in use but may be rotated at any other suitable speed depending upon the particular application. Other ways of driving rotation of the tissue-removing element 3 do not depart from the scope of the present invention. For example, it is contemplated that the catheter 2 could drive the tissue-removing element 3 in a rotational direction opposite the direction R, and the tissue-removing features of the tissue removing element would preferably be oriented in the opposite direction in such an embodiment.

Figure 4:
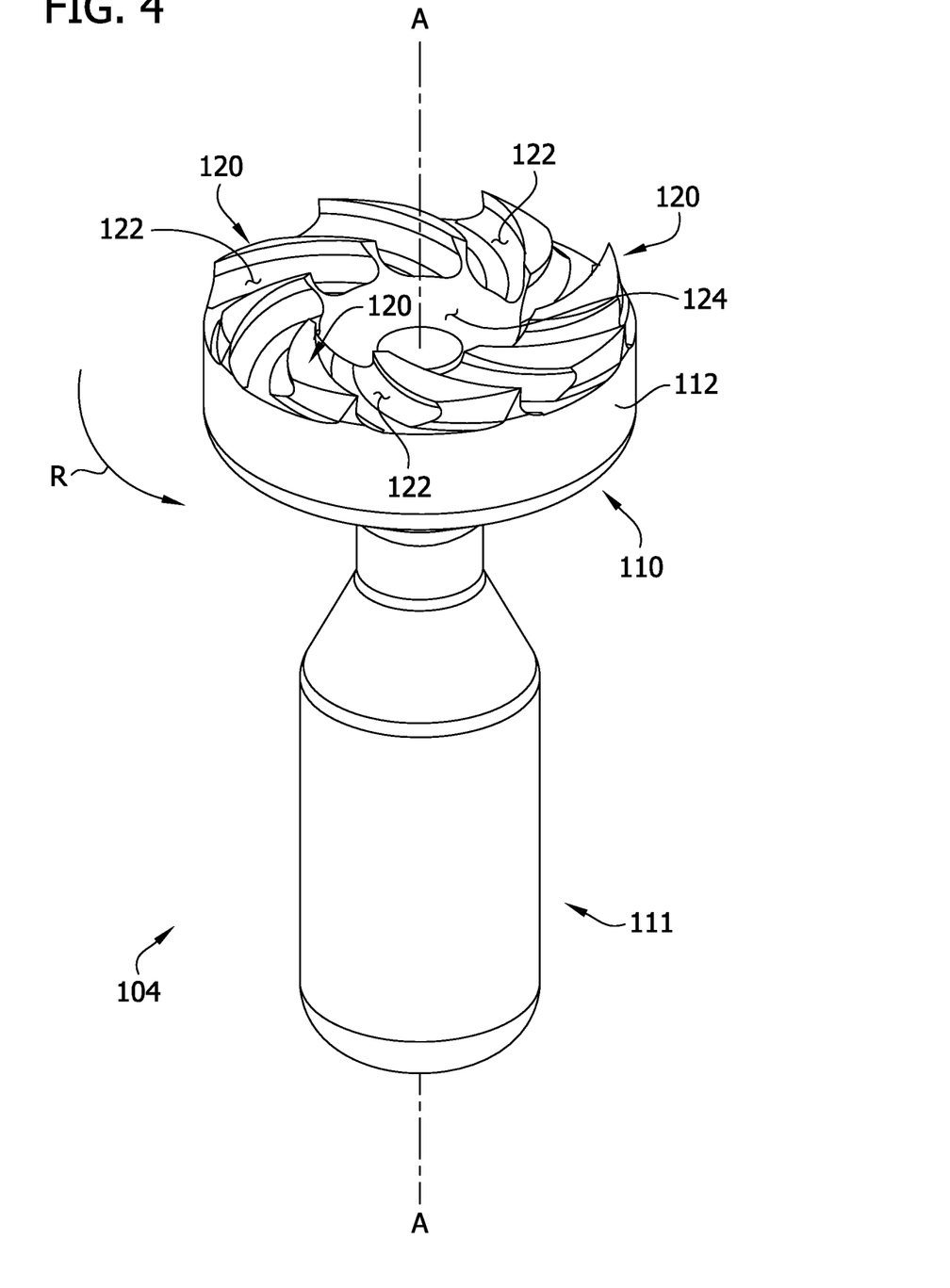
FIG. 4 is a perspective of the tissue-removing element.

Referring to FIG. 4, a first embodiment of a tissue-removing element suitable for use with the catheter 2 is generally indicated at reference number 104. The tissue-removing element 104 has proximal and distal axial ends (broadly, "first and second axial ends") spaced apart along an axis of rotation A. The tissue-removing element 104 includes a tissue-removing head, generally indicated at reference numeral 110, at the distal axial end thereof. A stem, generally indicated at reference numeral 111, connects the tissue-removing element to the drive shaft 20 for rotation about the axis of rotation A in a cutting direction R. In the illustrated embodiment, the tissue-removing element 104, including the tissue-removing head 110 and the stem 111, is formed from one unitary piece of material. In one or more embodiments, the one-piece tissue-removing element 104 can be made from one of 465 stainless steel, 17-4 stainless steel, MP35N alloy, 35N LT alloy, titanium, and blends thereof. Other materials, such as other types of stainless steel, nickel, cobalt, chromium molybdenum, plastic, or combinations thereof, can also be used without departing from the scope of the invention. As discussed in further detail below, the tissue-removing element 104 can be formed as one piece by removing material from a one-piece blank. The tissue-removing element may be formed in other ways and/or may be formed from more than one-piece of material without departing from the scope of the present invention.

The tissue-removing head 110 is sized and shaped to rotate in the cutting direction R as it advances axially through a body lumen to remove tissue from the body lumen. A generally axially extending outer radial surface 112 of the tissue-removing head 110 extends around the axis of rotation A at a radius sized to fit within the body lumen. The tissue-removing head 110 includes a plurality of axially (e.g., distally) extending projections, each generally indicated at reference numeral 120, spaced apart from one another around the axis of rotation A defining a plurality of channels 122 extending generally laterally relative to the axis of rotation between adjacent pairs of the projections. The tissue-removing head 110 further includes a radially inner, central cup-shaped recess 124. As discussed in greater detail below, the projections 120 form shearing members configured to remove tissue from a body lumen when the tissue-removing element 104 rotates in the cutting direction R and advances axially through the body lumen. The removed tissue passes generally inward through the channels 122 toward the central cup-shaped surface 124, which in turn directs the tissue toward the tissue-collection chamber 12.

The illustrated tissue-removing element 104 includes eight shearing members 120 that each extends generally inward from adjacent the outer radial surface 112 of the tissue-removing head 110. It will be understood that other numbers of shearing members (e.g., from about 2 shearing members to about 16 shearing members) can also be used without departing from the scope of the invention. The shearing members 120 are positioned spaced apart from one another about the axis of rotation A. In the illustrated embodiment, each of the eight shearing members 120 has a substantially identical shape. In alternative embodiments, the shearing members could have different shapes without departing from the scope of the invention.

Figure 5:
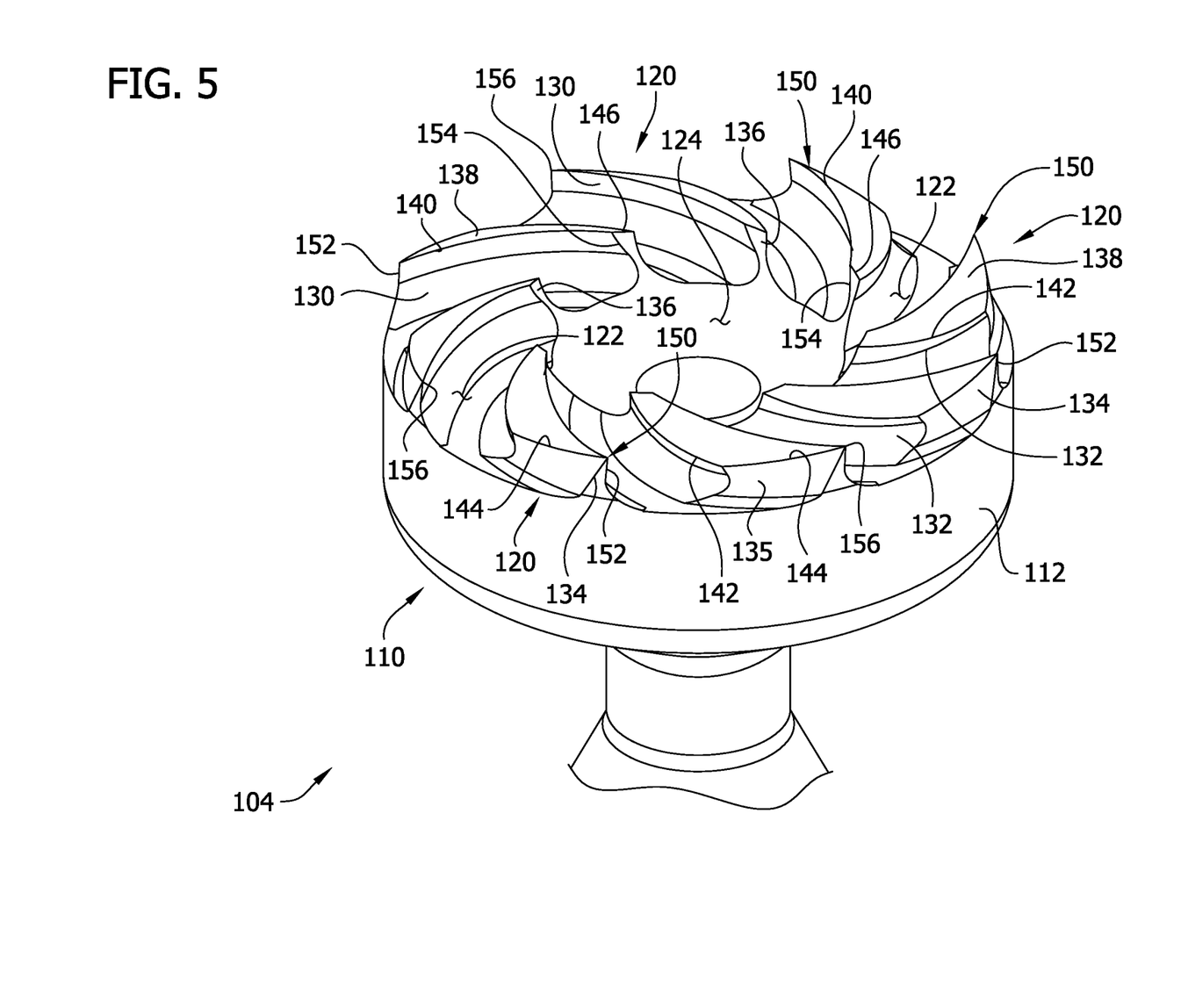
FIG. 5 is an enlarged fragmentary perspective of the tissue-removing element.

Referring to FIG. 5, each shearing member 120 includes a leading surface 130, a trailing surface 132, a radially outer surface 134, and a radially inner surface 136, each extending generally axially. An axial end surface 138 (e.g., a distal end surface) extends transverse to the leading surface 130, trailing surface 132, radially outer surface 134, and radially inner surface 136. The axial end surface 138 intersects the leading surface 130, trailing surface 132, radially outer surface 134, and radially inner surface 136, at a leading edge 140, trailing edge 142, radially outer edge 144, and radially inner edge 146, respectively. The leading surface 130 curves inwardly from the outer radial surface 112 of the tissue-removing head 110. Likewise, the trailing surface 132 curves inwardly from adjacent the outer radial surface 112 of the tissue-removing head 110. As discussed in further detail below, adjacent ones of the leading surfaces 130 and the trailing surfaces 132 each partially define a respective one of the channels 122, which also curve inwardly from the outer radial surface 112 of the tissue-removing head.

A radially outer portion of the leading surface 130 and a the radially outer surface 134 form a wedge portion, generally indicated at reference numeral 150, which is adapted to cleave tissue as the tissue-removing element 104 rotates in the body lumen in the cutting direction R. At the wedge portion 150 of the shearing member 120, the leading surface 130 and radially outer surface 134 form a wedge shape, which, as will be discussed in further detail below, is adapted to cleave tissue away from the body lumen wall. The radially outer surface 134 intersects the leading surface 130 at a tissue-cleaving edge 152 of the wedge portion 150. The tissue-cleaving edge 152, the leading surface 130, and the radially outer surface 134 form the wedge portion 150, which is a wedge-shaped formation pointed substantially in the cutting direction R. In the illustrated embodiment, the tissue-cleaving edge 152 extends generally axially. The leading surface 130 curves inward from the tissue-cleaving edge 152. A trailing portion 135 of the radially outer surface 134 curves slightly inward. The slight inward curvature of the trailing portion 135 of the radially outer surface 134 helps reduce frictional engagement between the radially outer surface and the cleaved tissue that engages the radially outer surface as the tissue-removing element rotates in the cutting direction R.

Figure 6:
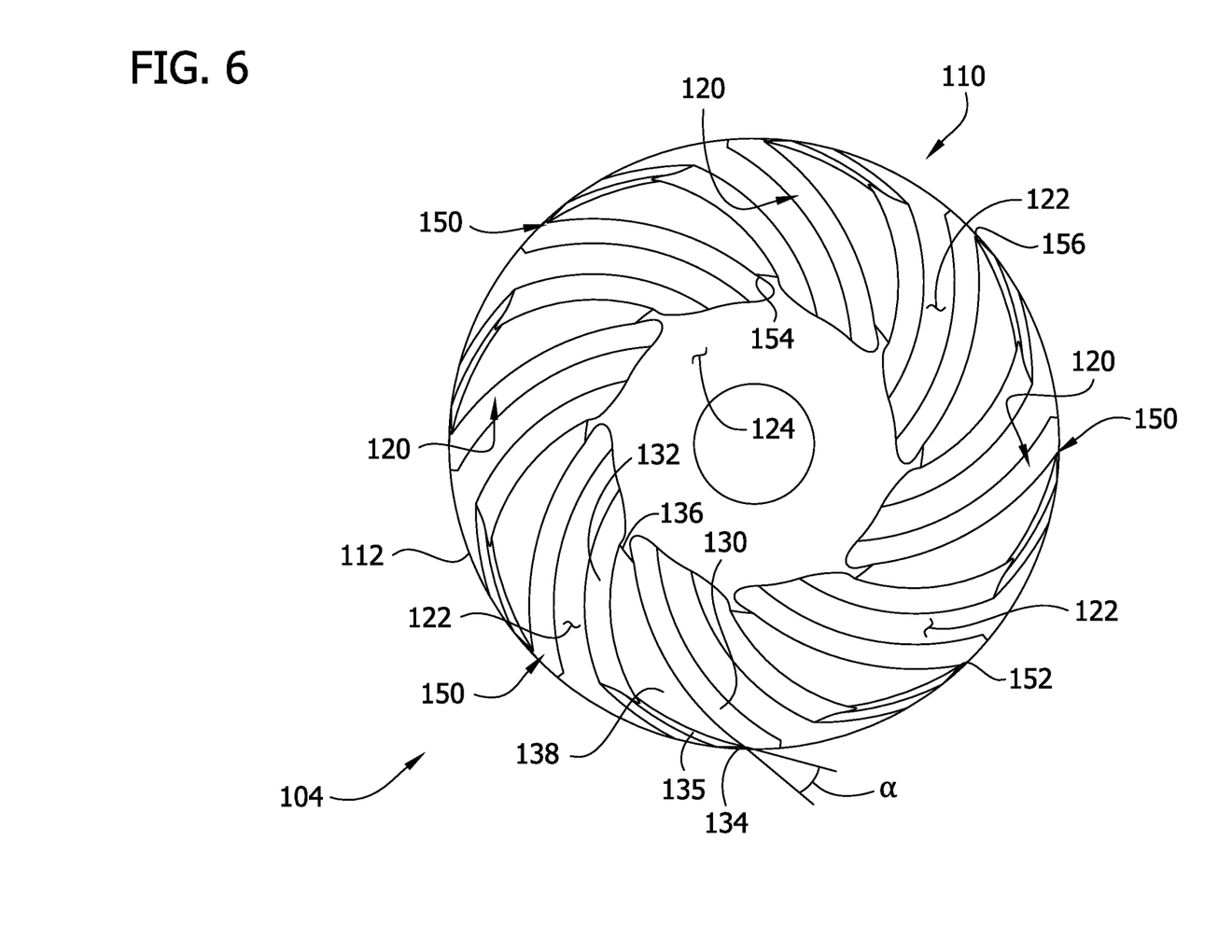
FIG. 6 is a top plan view of the tissue-removing element.

As shown in FIG. 6, the leading surface 130 and the radially outer surface 134 are oriented relative to one another at a wedge angle α (which, for clarity, is illustrated as the corresponding vertical angle of the actual wedge angle in FIG. 6) at the tissue-cleaving edge 152. In one or more preferred embodiments, the wedge angle α is between about 10° and about 75°. It will be understood that other wedge angles can also be used without departing from the scope of the invention. It is believed that a smaller wedge angle α improves the cleaving engagement of the wedge portion 150 with the tissue as compared with a shearing member 120. However, the improved engagement of a small wedge angle α must be balanced against a loss of robustness in the wedge portion 150 that is also an attendant effect of a smaller wedge angle. Robustness can be improved at the expense of engagement by increasing the wedge angle α.

Figure 7:
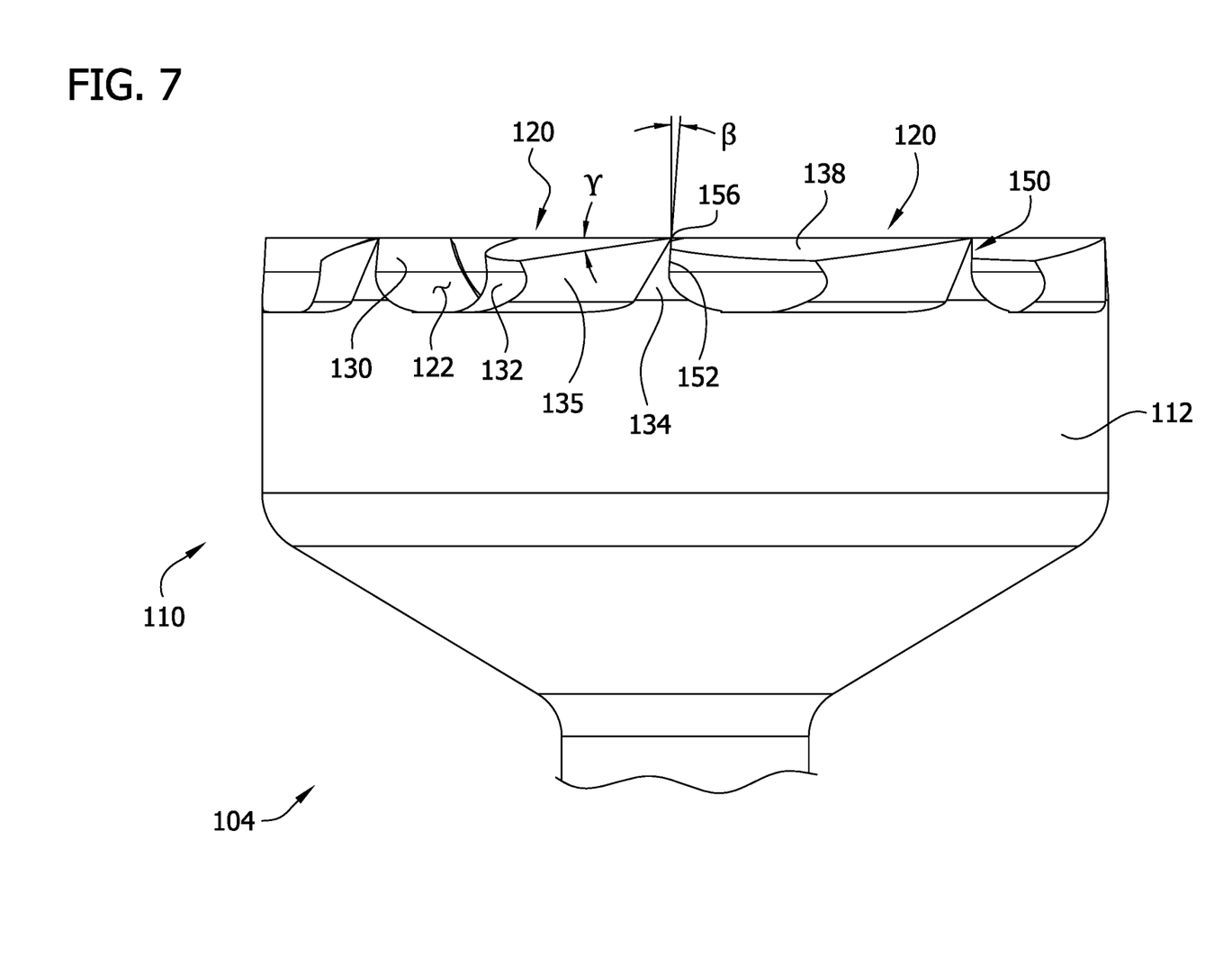
FIG. 7 is a fragmentary side elevation of the tissue-removing element.

Referring to FIG. 7, the tissue-cleaving edge 152 is oriented at a slight positive attack angle β (which, for clarity, is illustrated as the corresponding vertical angle of the actual attack angle in FIG. 7), which is defined as the angle of the tissue-cleaving edge with respect to a line parallel to the axis of rotation that passes through an axial tip 156 of the tissue-cleaving edge. The positive attack angle β results in an axial tip 156 that is proud of the tissue-cleaving edge 152. In one or more preferred embodiments, the tissue-cleaving edge 152 is oriented at an attack angle β of between about 0.5° and about 60°. It will be understood that other attack angles can also be used without departing from the scope of the invention. A larger positive attack angle β is believed to improve the engagement of the tissue-cleaving edge 152 with the tissue in the body lumen by enabling the tissue-cleaving edge to hook tissue and by reducing the reaction force of the tissue onto the tissue-removing element 104 as the tissue-removing element 104 rotates in the cutting direction R. However, it is also believed that a larger positive attack angle β reduces the robustness of the wedge portion 150 of the shearing member 120.

As the tissue-removing element 104 rotates in the cutting direction R in a body lumen, the tissue-cleaving edge 152 engages tissue in the body lumen, imparting stress on the tissue sufficient to indent, shear, cleave, or fracture the tissue. Initially, the axial tip 156 of the tissue-cleaving edge 152 engages the tissue, and subsequently the more proximal portions of the tissue-cleaving edge 152 engage the tissue. Further rotation of the tissue-removing element 104 drives the tissue-cleaving edge 152 more deeply into the tissue, causing the leading surface 130 and radially outer surface 134 of the wedge portion 150 to impart opposing forces on tissue positioned on opposite sides of the wedge portion. The opposing forces cleave the tissue, and, as discussed in further detail below, the leading surface 130 shears a portion of the cleaved tissue radially inwardly through the adjacent channel 122 and toward the cup-shaped recess 124.

Referring again to FIG. 5, the leading surface 130 of the shearing member 120 is shaped and arranged to shear at least a portion of the tissue cleaved by the wedge portion 150 radially inward as the tissue-removing element 120 rotates in the cutting direction R. The leading surface 130 of the shearing member 120 is concave (in the axial direction) and curves inwardly from the tissue-cleaving edge 152 and intersects the radially inner surface 136 at an inner, leading edge 154. It is also contemplated that in some embodiments, the leading surface 130 will intersect the trailing surface of the shearing member at a radially inner edge such that the shearing member will not have an inner surface of substantial width. The radially inward portion of the leading surface 130 trails a radius of the tissue-removing element 104 that intersects the tissue-cleaving edge 152 thereof. For the entire curved radial dimension of the leading surface 130, between the tissue-cleaving edge 152 and the inner, leading edge 154, the leading surface is configured to engage tissue at an obtuse angle as the tissue-removing element rotates in the cutting direction R. As a result, engagement between the tissue and the leading surface 130 of the shearing member 120 shears the tissue radially inward at all points along its curved radial dimension. Moreover, the curved shape of the leading surface 130 shears the tissue inwardly through the adjacent channel 122 and into the cup-shaped recess 124.

Referring again to FIG. 7, the axial end surface 138 of the illustrated shearing member 120 is formed at a positive relief angle γ. The relief angle γ is defined as an angle between the axial end surface and a plane perpendicular to the axis of rotation A that intersects the leading edge 140 where the angle is measured. As illustrated in FIG. 7, an axial end surface 138 with a positive relieve angle γ is positioned below (i.e., proximal of) the plane perpendicular to the axis of rotation A. In one or more preferred embodiments, the relief angle γ is an angle of from about 0.5° to about 60°. However, other relief angles can also be used without departing from the scope of the invention. A larger positive relief angle is thought to reduce interference and frictional engagement between the axial end surface 138 and the tissue in the body lumen as the tissue-removing element 104 rotates in the cutting direction R and advances axially through the body lumen. Engagement between the axial end surface 138 and the tissue in the body lumen is not thought to significantly enhance tissue removal. Thus, by minimizing the amount of force spent overcoming frictional engagement between the axial end surface 138 and the tissue (e.g., by increasing the relief angle of the axial end surface), more of the force imparted on the shearing member 120 can be used to remove tissue, which improves the overall cutting efficiency of the tissue-removing element 104. This improvement in efficiency from an increased relief angle γ may be balanced against the loss in robustness of the shearing member 120 which is an attendant consequence of removing material from the shearing member to increase the relief angle.

The axial end surface 114 of the tissue-removing head 110 defines a plurality of channels 122 alternating with the shearing members 120 around the axis of rotation A of the tissue-removing element 104. As discussed above, the leading surface 130 of a shearing member 120 and the trailing surface 132 of an adjacent shearing member each partially define one of the channels 122. Like the leading and trailing surfaces 130, 132, each of the channels 122 curves inwardly from the outer radial surface 112 of the tissue-removing head 110. Each of the channels 122 extends inward through the outer radial surface 112 of the tissue-removing head 110. Each of the channels 122 acts as a tissue passage for carrying tissue sheared by the shearing members 122 toward the cup-shaped recess 124 at the center of the tissue-removing head. As the leading surfaces 130 of the shearing members 120 engage tissue in the body lumen and shear the tissue inwardly, the sheared tissues travel through the channels 122 toward the cup-shaped recess 124 at the center of the tissue-removing head. The channels 122 are configured to direct substantially all of the tissue removed from the body lumen by the tissue-removing element 104 toward the cup-shaped recess 124, including the portion of the tissue that is engaged at the radially outward-most portion of the tissue-removing head 110.

The cup-shaped recess 124 of the tissue-removing head 110 is adapted to direct tissue toward the tissue collection chamber 12 (e.g., in the distal direction) as the tissue-removing element 104 advances axially through the body lumen. The radially inner surfaces 136 of the shearing members 120 partially define an axially extending annular boundary of the cup-shaped recess 124. The channels 122 extend radially inwardly through the annular boundary. Thus, the channels 122 are in communication with and open to the cup-shaped recess 124 to form a pathway for delivering sheared tissue to the cup-shaped recess. As the tissue-removing element 104 rotates in the cutting direction R and advances axially through the body lumen, the radially inner surfaces 136 of the shearing members 120 tend to direct the tissue in the cup-shaped recess 124 toward the tissue collection chamber 12.

In one or more exemplary methods of making the tissue-removing element 104, the tissue-removing element can be formed by removing material from a blank comprising a single piece of material using one or more cutting implements. In one or more embodiments, a blank comprises a generally cylindrical body of material with opposite first and second axial ends and an axis extending between the axial ends. In certain embodiments, only an axial end portion at the first axial end of the blank is cylindrical. Thus, the blank can be preformed to have the shape of the stem 111 of the tissue-removing element 104 or can be machined to form the shape of the proximal end portion of the tissue-removing element 104 as part of a method of making a tissue-removing element without departing from the scope of the invention.

In one method of making the tissue-removing element 104, a cutting implement, such as a milling cutter of a multi-axis mill or Swiss machine, removes material from the blank to form the shearing members 120. A cutting implement preferably removes material from the blank to form at least a leading surface 130, trailing surface 132, radially inner surface 136, and axial end surface 138 to form one of the shearing members 120. In the illustrated embodiment, a cutting implement also removes material from the blank to form the inwardly curving trailing portion of the radially outer surface 134. In certain embodiments, a single cutting implement can be used to form each of the leading surface 130, trailing surface 132, radially inner surface 136, and axial end surface 138, respectively, by passing the cutting implement along a cutting path for the respective surface. In one or more embodiments, the leading surface 130 of one shearing member and the trailing surface 132 of an adjacent shearing member 120 are formed together in one pass of a cutting implement along a cutting path. In certain embodiments, each of the channels 122 is formed by removing material from the blank by passing the cutting implement along a cutting path. More specifically, the channels 122 can be sequentially formed by passing the cutting implement along a cutting path to form one channel, rotating the blank about the axis of rotation A (e.g., one-eighth of one rotation) with respect to the cutting implement, and passing the cutting implement along the cutting path again to form another channel. This sequence can be repeated until each of the channels 122 has been formed in the tissue-removing head 110. In addition to the shearing members 120 and channels 122, the cup-shaped recess 124 can also be formed by removing material from the blank.

An exemplary method of using the catheter 2 to remove tissue from a body lumen will now be described. A user inserts the catheter 2 into the body lumen (such as by using a guidewire and an introducer sheath), positions the tissue-removing element 104 in the deployed position, and rotates the tissue-removing element in the cutting direction R as the catheter advances axially through the lumen. As the tissue-removing element 104 rotates in the cutting direction R, the axial tip 156 of the tissue-cleaving edge 152 of one of the shearing members 120 engages the tissue and forms an incision in the tissue. The tissue-cleaving edge 152 remains engaged with the incision in the tissue and enlarges the incision as the tissue-removing element 104 continues to rotate. The wedge portion 150 of the shearing member 120 cleaves the tissue inward against the leading surface 130 of the shearing member. The leading surface of the 130 of the shearing member 120 continues to shear the cleaved tissue inwardly through the adjacent channel 122 until the tissue passes through the annular boundary of the cup-shaped recess 124. The cup-shaped recess 124, together with the force of tissue entering the cup-shaped recess 124 from adjacent and opposite channels, directs the sheared tissue distally into the tissue collection chamber 12, which stores the removed tissue until the catheter 2 is removed from the body lumen. The tissue-collection chamber 12 can be flushed or cleaned when it is filled with removed tissue.

Figure 8:
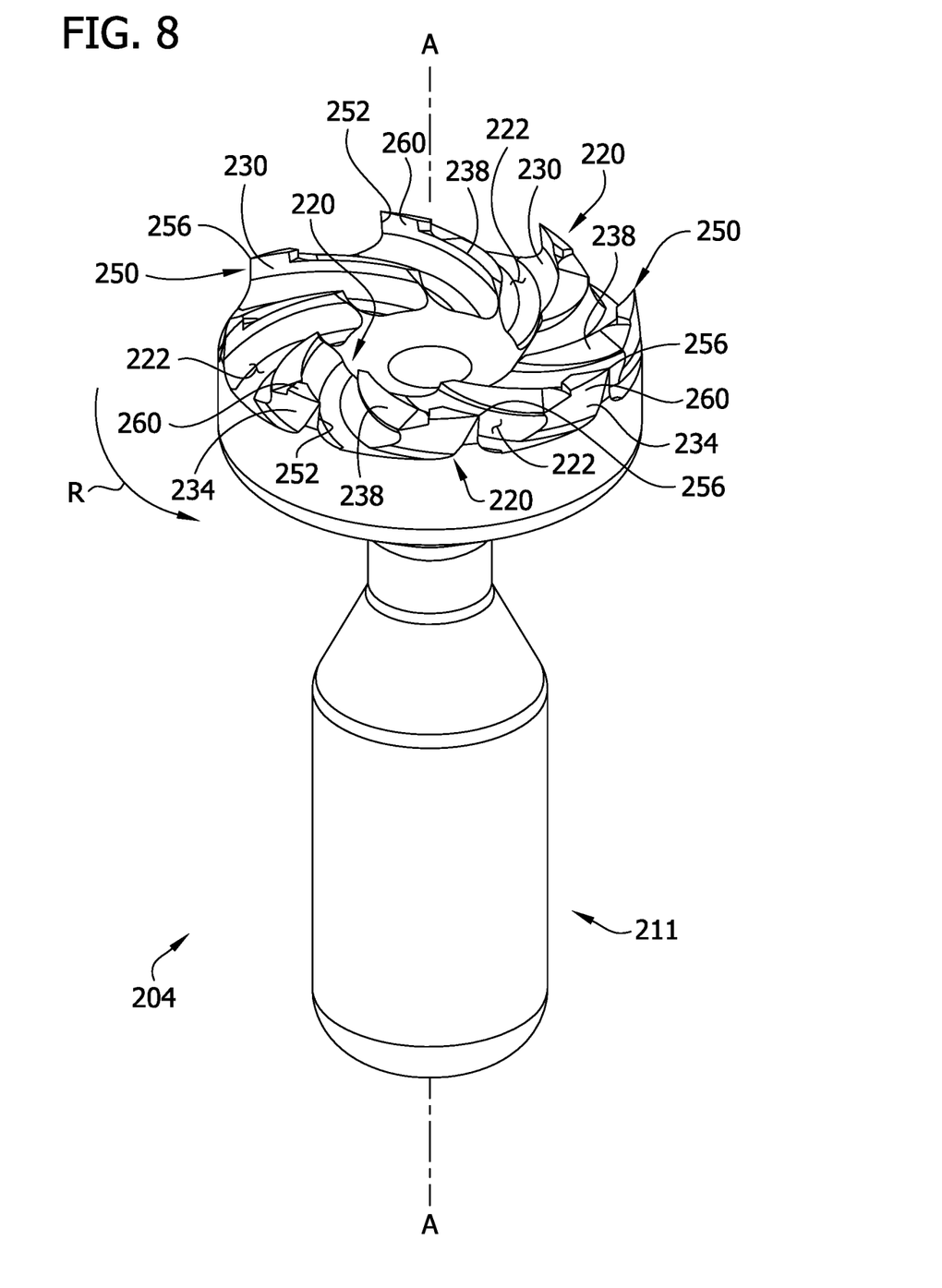
FIG. 8 is a perspective of another tissue-removing element.
Figure 9:
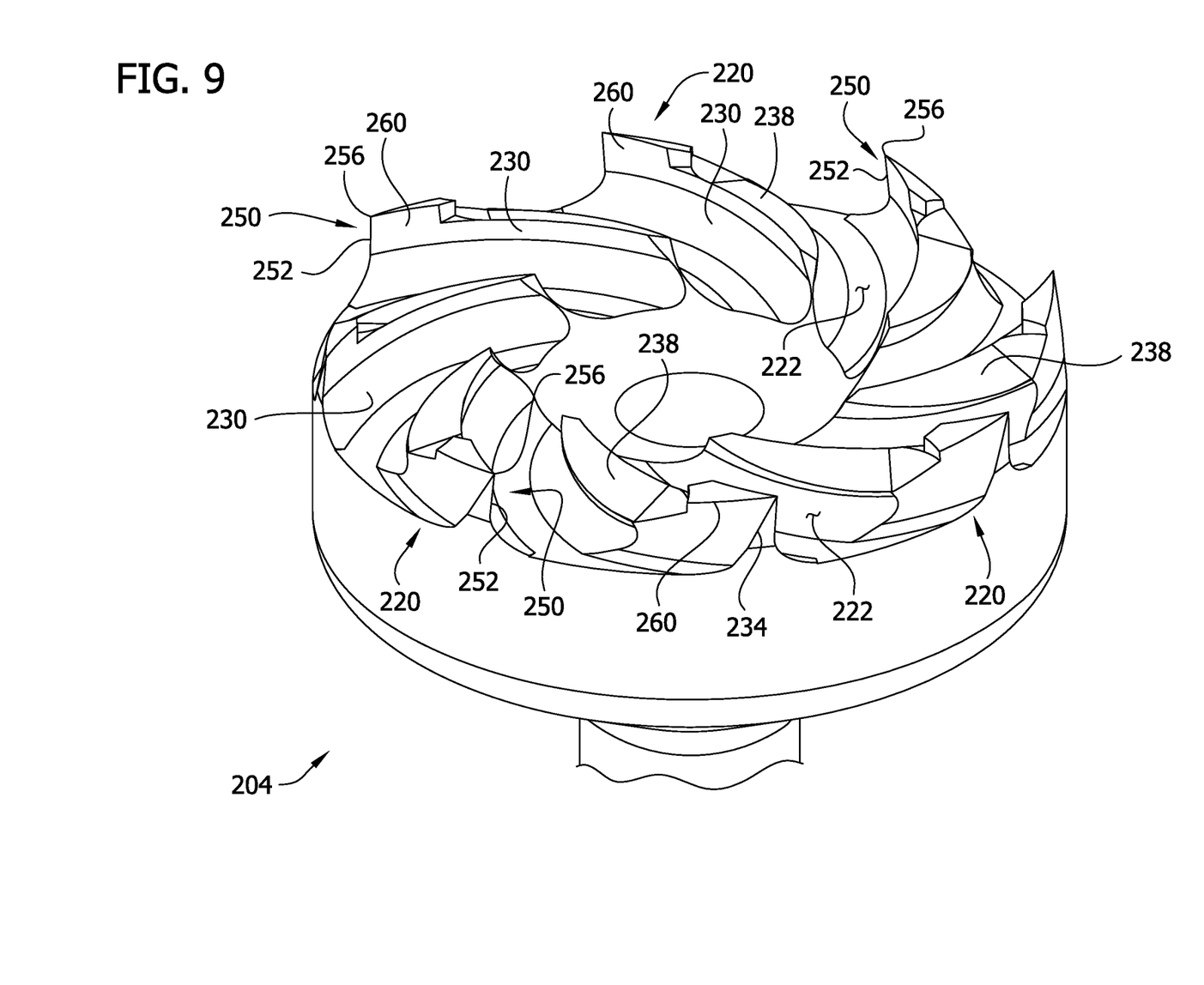
FIG. 9 is an enlarged fragmentary perspective of the tissue-removing element of FIG. 8.

Referring to FIG. 8, another embodiment of a tissue-removing element is generally designated by reference number 204. The tissue-removing element 204 is substantially similar to the tissue-removing element 104, except for the differences that are, in part, apparent and, in part, pointed out hereinafter. Features of the tissue-removing element 204 are given the reference number of corresponding features of the tissue-removing element 104, plus 100. Like the tissue-removing element 104, the tissue-removing element 204 includes a stem 211 configured for operative connection with the drive shaft 20 of the catheter 12 for rotation about an axis of rotation A in a cutting direction R. In addition, like the tissue-removing element 104, the tissue-removing element 204 includes eight shearing members 220 and eight channels 222 extending between adjacent pairs of the shearing members. Other numbers of shearing members and channels can also be used without departing from the scope of the invention. Each of the shearing members 220 has a leading surface 230 and a radially outer surface 234 that intersect one another at a tissue-cleaving edge 252 and form wedge portion 250 adapted to cleave tissue as the tissue-removing element 204 rotates in the cutting direction R. However, as shown in FIG. 9, unlike the tissue-removing element 104, the wedge portion 250 of each shearing member 220 (i.e., the radially outer portion of the shearing member 220) comprises an axially (e.g., distally) extending projection 260 that protrudes axially (e.g., distally) from the axial end surface 238 of the shearing member.

The axially extending projection 260 shifts the location of the axial tip 256 of the wedge portion 250 distally, for example, as compared to the axial tip 156 of the wedge portion 150. The axial tip 256 is positioned proud of all other portions of the shearing member 220. As the tissue-removing element 204 rotates in the cutting direction R, the raised axial tip 256 engages tissue in the body lumen and imparts a large amount of stress on the tissue. It is believed that, the proud-positioned axial tip 256 is capable of imparting sufficiently large stresses upon hard tissue to cause the tissue to fracture. In addition, intact tissue continues to impart a force on the radially inward facing surface of the wedge portion 250 that helps maintain engagement between the tissue-removing element 204 and the tissue. In the illustrated embodiment the portion of the axial end surface 238 at the axially extending projection 260 has a lesser relief angle than the portions of the axial end surface radially inward thereof. The lesser relief strengthens the construction of the axially extending projection 260 so that it can withstand the impacts between the axial tip 256 and the tissue as the tissue-removing element 204 rotates in the cutting direction R. But the axial end surface 238 could have a greater relief angle without departing from the scope of the invention.

In a preferred embodiment, the tissue-removing element 204, like the tissue-removing element 104, is made from a single unitary piece of material. A suitable method of making the tissue-removing element 204 is substantially similar to the method of making the tissue-removing element 104, discussed above. However, additional passes of the cutting implement may be required to form the axially extending projection 260.

Figure 10:
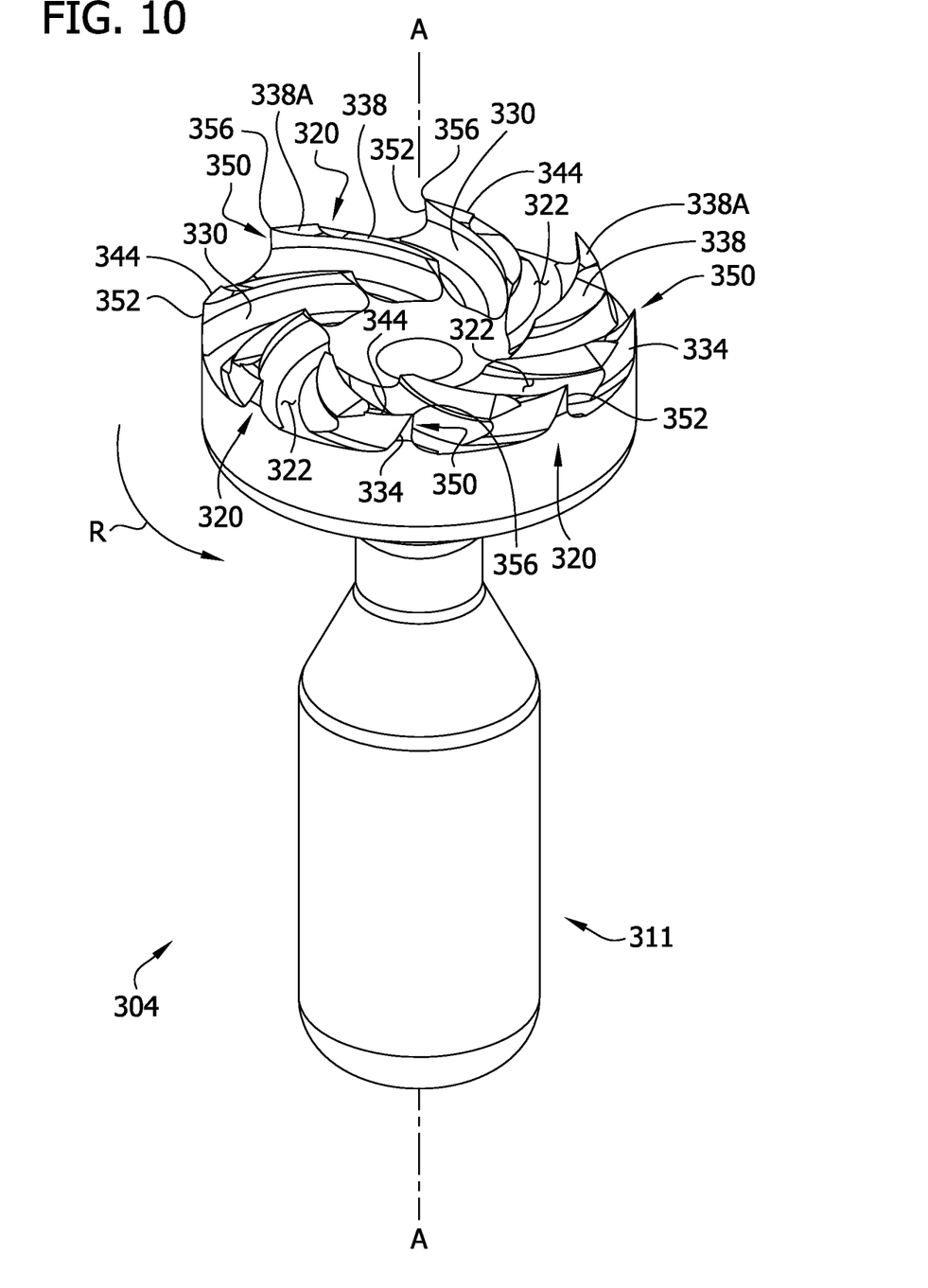
FIG. 10 is a perspective of another tissue-removing element.
Figure 11:
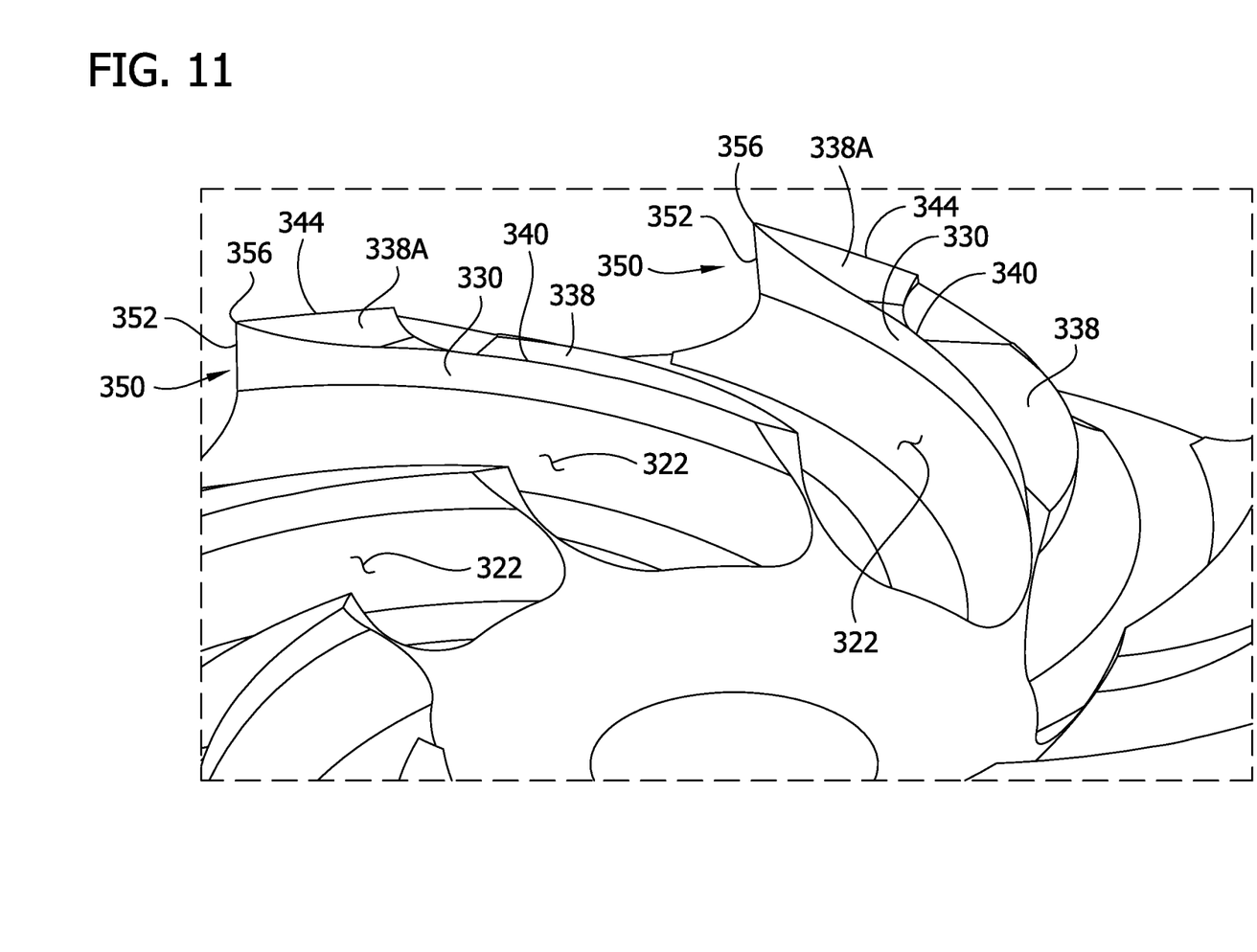
FIG. 11 is an enlarged view of a portion of FIG. 10.

Referring to FIG. 10, another embodiment of a tissue-removing element is generally designated by reference number 304. The tissue-removing element 304 is substantially similar to the tissue-removing element 104, except for the differences that are, in part, apparent and, in part, pointed out hereinafter. Features of the tissue-removing element 304 are given the reference number of corresponding features of the tissue-removing element 104, plus 200. Like the tissue-removing element 104, the tissue-removing element 304 includes a stem 311 configured for operative connection with the drive shaft 20 of the catheter 12 for rotation about an axis of rotation A in a cutting direction R. In addition, like the tissue-removing element 104, the tissue-removing element 304 includes eight shearing members 320 and eight channels 322 extending between adjacent pairs of the shearing members. Other numbers of shearing members and channels can also be used without departing from the scope of the invention. Each of the shearing members 320 has a leading surface 330 and a radially outer surface 334 that intersect one another at a tissue-cleaving edge 352 and form wedge portion 350 adapted to cleave tissue as the tissue-removing element 304 rotates in the cutting direction R. However, as shown in FIG. 11, unlike the tissue-removing element 104, a radially outer portion 338A of the axial end surface 338 slopes such that the radially outer edge 344 forms a tissue slicing edge adapted to slice through tissue as the tissue-removing element 304 rotates in the cutting direction R.

Whereas the entire axial end surface 138 of the shearing member 120 slopes in the trailing direction, the radially outer portion 338A of the axial end surface 338 of the shearing member 320 slopes in the leading direction. Thus, a portion of the radially outer edge 344 is proud of the leading edge 340. In the illustrated embodiment the radially outer portion 338A of the axial end surface 338 is slightly curved. However, it could also be planar or more substantially curved without departing from the scope of the invention. As the tissue-removing element 304 rotates in the cutting direction R, the axial tip 356 engages the tissue before any other portion of the shearing member 320. The leading surface 330 of the shearing member 320 engages tissue radially inward of the wedge portion 350 and shears that tissue radially inwardly. In addition, as the tissue-removing element 304 rotates in the cutting direction R and advances axially through the body lumen, the tissue-slicing edge 344 slices through tissue adjacent the radially outer portion 338A of the axial end surface 338.

In a preferred embodiment, the tissue-removing element 304, like the tissue-removing element 104, is made from a single unitary piece of material. A suitable method of making the tissue-removing element 304 is substantially similar to the method of making the tissue-removing element 104, discussed above. However, additional passes of the cutting implement may be required to form the leading portion 338A of the axial end surface 338 and the tissue-slicing edge 362.

Where dimensional ranges are cited in the present disclosure, it should be understood that the range is inclusive of the end points of the range, unless otherwise indicated. For example, a range of "between about 1 inch and about 2 inches" includes lengths of about 1 inch and about 2 inches and all of the lengths between those two end points of the range.

When introducing elements of the present invention or the one or more embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above apparatuses, systems, and methods without departing from the scope of the invention, it is intended that all matter contained in the above description and shown in the accompanying drawings shall be interpreted as illustrative and not in a limiting sense.

Having described the invention in detail, it will be apparent that modifications and variations are possible without departing from the scope of the invention defined in the appended claims.

What is claimed is:

1. A tissue-removing catheter for removing tissue from a body lumen, the tissue-removing catheter comprising:
   a rotatable shaft; and
   a tissue-removing element coupled to the rotatable shaft for rotating the tissue-removing element in a cutting direction about an axis of rotation, the tissue-removing element comprising a tissue-removing head having an outer radial surface extending around the axis of rotation, the tissue-removing head including a plurality of shearing members extending inward from the outer radial surface and being spaced apart from one another around the axis of rotation, each shearing member having a leading surface curving inward from the radially outer surface,
   wherein the tissue-removing head has a distal axial end surface that defines a plurality of channels alternating with the shearing members around the axis of rotation, each of the channels having an open outer radial end extending inward through the outer radial surface of the tissue-removing head, an open inner radial end adjacent the axis of rotation, and a length extending between the open outer and inner radial ends; and
   wherein each of the plurality of channels has a proximal axial end and a second distal axial end spaced apart along the axis of rotation and extending along the respective length of the channel, the proximal axial end of each channel being closed and bounded by the distal axial end surface of the tissue-removing head, the distal axial end being open to allow tissue removed by the tissue-removing element to enter the channel.

2. A tissue-removing catheter as set forth in claim 1, wherein each of the channels curves inward from the radially outer surface.

3. A tissue-removing catheter as set forth in claim 1, wherein the leading surface of each shearing member partially defines an adjacent one of the plurality of channels.

4. A tissue-removing catheter as set forth in claim 1, wherein each of the shearing members has a radially outer surface that intersects the respective leading surface at a tissue-cleaving edge.

5. A tissue-removing catheter as set forth in claim 4, wherein the leading surface of each shearing member has a leading portion, wherein the tissue-cleaving edge and the leading portion of the leading surface and the radially outer surface of each shearing member form a wedge portion adapted to cleave tissue in the body lumen as the tissue-removing element rotates in the cutting direction.

6. A tissue-removing element as set forth in claim 5, wherein the leading surface of each shearing member is shaped and arranged to shear at least a portion of the cleaved tissue radially inward as the tissue-removing element rotates in the cutting direction.

7. A tissue-removing catheter as set forth in claim 4, wherein the tissue-cleaving edge of each shearing member is radially aligned with the outer radial surface of the tissue-removing head.

8. A tissue-removing catheter as set forth in claim 4, wherein each of the shearing members has a trailing surface curving inward from adjacent the radially outer surface of the tissue-removing head.

9. A tissue-removing catheter as set forth in claim 8, wherein the trailing surface of each shearing member partially defines an adjacent channel.

10. A tissue-removing catheter as set forth in claim 8, wherein each shearing member comprises an axial end surface intersecting the leading and trailing end surfaces of the respective shearing member at leading and trailing edges, respectively.

11. A tissue-removing catheter as set forth in claim 10, wherein a radially outer portion of the axial end surface of each of the shearing members is raised axially relative a radially inward portion of the axial end surface.

12. A tissue-removing catheter as set forth in claim 10, wherein a radially outer portion of the axial end surface of each of the shearing members slopes such that a portion of the radially outer edge forms a tissue-slicing edge adapted to slice through tissue as the tissue-removing element rotates in the cutting direction.

13. A tissue-removing catheter as set forth in claim 4, wherein a radially inward portion of the leading surface of each shearing member trails a radius of the tissue-removing element that intersects the tissue-cleaving edge thereof.

14. A tissue-removing catheter as set forth in claim 13, wherein the leading surface is shaped and arranged to engage tissue at an obtuse angle along its entire radial dimension.

15. A tissue-removing catheter as set forth in claim 1, wherein a radially central region of the tissue-removing head defines a cup-shaped recess.

16. A tissue-removing catheter as set forth in claim 15, wherein each of the shearing members comprises a radially inner surface, the radially inner surfaces of the shearing members partially defining an annular boundary of the cup-shaped recess.

17. A tissue-removing catheter as set forth in claim 16, wherein each of the channels extends inward through the annular boundary of the cup-shaped recess.

* * * * *